United States Patent
Skinner et al.

(10) Patent No.: US 10,976,241 B2
(45) Date of Patent: Apr. 13, 2021

(54) METHODS OF ASSESSING ANTIBODY-DRUG CONJUGATES

(71) Applicant: Regeneron Pharmaceuticals, Inc., Tarrytown, NY (US)

(72) Inventors: Andria Skinner, Mohegan Lake, NY (US); Natallia Kulyba, Selkirk, NY (US)

(73) Assignee: Regeneran Pharmaceuticals, Inc., Tarrytown, NY (US)

(*) Notice: Subject to any disclaimer, the term of this patent is extended or adjusted under 35 U.S.C. 154(b) by 172 days.

(21) Appl. No.: 16/121,909

(22) Filed: Sep. 5, 2018

(65) Prior Publication Data
US 2019/0079005 A1  Mar. 14, 2019

Related U.S. Application Data

(60) Provisional application No. 62/566,153, filed on Sep. 8, 2017.

(51) Int. Cl.
| | |
|---|---|
| *G01N 21/31* | (2006.01) |
| *G01N 33/68* | (2006.01) |
| *G01N 30/02* | (2006.01) |
| *A61K 47/68* | (2017.01) |
| *G16B 5/00* | (2019.01) |
| *G16C 20/30* | (2019.01) |
| *G01J 3/427* | (2006.01) |
| *G01N 21/27* | (2006.01) |
| *G01N 30/88* | (2006.01) |
| *G01N 21/33* | (2006.01) |
| *B01D 15/34* | (2006.01) |

(52) U.S. Cl.
CPC ..... *G01N 21/3103* (2013.01); *A61K 47/6803* (2017.08); *G01J 3/427* (2013.01); *G01N 21/27* (2013.01); *G01N 21/314* (2013.01); *G01N 30/02* (2013.01); *G01N 33/6854* (2013.01); *G16B 5/00* (2019.02); *G16C 20/30* (2019.02); *B01D 15/34* (2013.01); *G01N 21/33* (2013.01); *G01N 2021/3129* (2013.01); *G01N 2030/8813* (2013.01)

(58) Field of Classification Search
None
See application file for complete search history.

(56) References Cited

U.S. PATENT DOCUMENTS

| | | | |
|---|---|---|---|
| 2012/0130649 A1 | 5/2012 | Salerno et al. | |
| 2015/0198573 A1* | 7/2015 | Habel | G01N 30/8682 702/50 |

OTHER PUBLICATIONS

Gupta, N. et al. Development of a facile antibody-drug conjugate platform for increased stability and homogeneity, Chemical Science, vol. 8, pp. 2387-2395 (Year: 2017).*
Hamblett, K.J. et al. Effects of Drug Loading on the Antitumor Activity of a Monoclonal Antibody Drug Conjugate, Clinical Cancer Research, vol. 10, pp. 7063-7070 (Year: 2004).*
Adler et al., "Therapeutic antibodies against cancer," Hematol Oncol Clin North Am., Jun. 2012; 26(3):447-481.
Bouchard et al., "Antibody-drug conjugates—a new wave of cancer drugs," Bioorganic Med. Chem. Lett. 24: 5357-5363 (2014).
Boylan et al., "Conjugation Site Heterogeneity Causes Variable Electrostatic Properties in Fc Conjugates," Bioconjugate Chem., 2013, 24, 1008-1016.
Chen, "Drug-to-antibody ratio (DAR) by UV/Vis spectroscopy," Methods Mol. Biol. 1045:267-73 (2013).
Greenfield et al., "Evaluation in Vitro of Adriamycin Immunoconjugates Synthesized Using an Acid-sensitive Hydrazone Linker," Cancer Research, Oct. 15, 1990, 30, 6600-6607.
Hamann et al., "An anti-CD33 Antibody-Calicheamicin Conjugate for Treatment of Acute Myeloid Leukemia. Choice of Linker," Bioconjugate Chem., 2002, 13, 40-46.
Hamblett et al., "Effects of Drug Loading on the Antitumor Activity of a Monoclonal Antibody Drug Conjugate," Clinical Cancer Research, Oct. 2004; 10:7063-7070.
Hinman et al., "Preparation and Characterization of Monoclonal Antibody Conjugates of the Calicheamicins: A Novel and Potent Family of Antitumor Antibiotics," Cancer Research, Jul. 15, 1993; 53:3336-3342.
Li et al., "Monoclonal antibody-related drugs for cancer therapy," Drug Discoveries & Therapeutics, 2013; 7(5):178-184.
Sassoon et al., "Antibody-Drug Conjugate (ADC) Clinical Pipeline: A Review," Methods Mol. Biol., 1045:1-27 (2013).
Scott et al., "Monoclonal antibodies in cancer therapy," Cancer Immunity, May 2012, 12:14.
Sliwkowski et al., "Antibody therapeutics in cancer," Science, Sep. 13, 2013, 341:1192-1198.
Hooijschuur, "UV-Vis Spectrometry Basics," Chromedia Analytical Sciences, 2020, 3 pages, retrieved from https://www.chromedia.org/chromedia?waxtrapp=fotjtbEsHiemBpdmBIIEcCAtB&subNav=lnijabEsHiemBpdmBIIEcCAtBN on Nov. 5, 2020.

* cited by examiner

*Primary Examiner* — Xiaoyun R Xu
(74) *Attorney, Agent, or Firm* — Cooley LLP; Matthew Pavao; Ivor R. Elrifi

(57) ABSTRACT

The present disclosure provides methods of assessing DAR of ADC products that provide advantages over known methods. Specifically, methods of the disclosure can be used in high-throughput applications and/or without having to dilute ADC samples during the assessment.

18 Claims, No Drawings

METHODS OF ASSESSING ANTIBODY-DRUG CONJUGATES

CROSS REFERENCE TO RELATED APPLICATIONS

This application claims priority to and the benefit of U.S. Provisional Application Ser. 62/556,153, filed Sep. 8, 2017, which is herein incorporated by reference in its entirety.

BACKGROUND

Antibody-drug-conjugates (ADCs) are an emerging class of drug molecules. Their ability to locate to a specific target and deliver a potent drug makes them an attractive option for developing a target based therapeutic product. ADCs are produced by chemically linking potent drug molecules to a monoclonal antibody via a selected chemical linker. The average number of drug molecules that are conjugated to the monoclonal antibody is called drug-to-antibody ratio, ("DAR"). DAR is an important quality attribute of ADC products, because it can impact product efficacy, safety and/or stability. Accordingly, methods of assessing DAR of ADC products in a reliable and high throughput manner are desirable.

DETAILED DESCRIPTION

The present disclosure provides methods of assessing DAR of ADC products that provide advantages over known methods. Specifically, methods of the disclosure can be used in high-throughput applications and/or without having to dilute ADC samples during the assessment.

UV-Vis and Beer-Lambert's Law

DAR has traditionally been measured using UV-Vis spectroscopy (see, e.g., Chen, Methods Mol. Biol. 1045:267-73 (2013)). The basis for this analysis is the Beer-Lambert law, a direct proportional relationship between the absorbance and concentration of a substance:

$$A=\varepsilon cl,$$

where $A$ is the absorbance, $\varepsilon$ is the extinction coefficient (a physical constant of the substance), $l$ is the path length through the cell containing the analyte, and $c$ is the concentration.

DAR measurement for an ADC product using UV-Vis spectroscopy relies on the difference in absorption maxima for the antibody (e.g., 280 nm) and the absorption maxima for the drug (e.g., at 252 nm). For example, the average DAR can be calculated using the difference in the measured absorption at 280 nm and 252 nm for the conjugated material. Although the UV-Vis method is widely used in industry, it lacks the throughput needed for formulation screening studies. It also cannot be used without sample dilution, leading to errors associated with sample dilution.

The present disclosure is thus based, at least in part, on alternative methods for measuring DAR using size exclusion chromatography (e.g., UPLC) and slope spectroscopy. These methods were characterized and compared to UV-Vis spectroscopy with respect to reproducibility, precision and sensitivity. The data generated support use of UPLC-based DAR methods to overcome the throughput limitations of traditional UV-Vis methods. Further, the slope spectroscopy based method can be used to analyze ADC samples without sample dilution.

UPLC-Based Methods

In one embodiment, size exclusion is used to determine DAR. In some embodiments, the methods disclosed herein comprise applying a sample comprising an antibody-drug conjugate to a size-exclusion chromatography matrix. In some embodiments, the methods disclosed herein comprise applying to and running a sample comprising an antibody-drug conjugate through a size-exclusion chromatography matrix. In some embodiments, a total amount of ADC sample is applied to a size exclusion matrix for analysis. For example, the following UPLC-based methodology was used to assess DAR.

| | |
|---|---|
| Column: | Waters Acquity UPLC BEH200 SEC (Part# 186005225) 4.6 mm × 15 cm, 1.7 μm particle size, max pressure: 1034 bar 2 columns attached inline |
| Mobile Phase: | Perchlorate SEC Buffer: 10 mM Phosphate, pH 6.0 1M NaClO$_4$ |
| Gradient Info: | Isocratic |
| Flow Rate: | 0.4 mL/min |
| Method Run Time: | 12 minutes |
| Column Temperature: | Not controlled |
| Wavelength of Detection | 280 nm and 252 nm (or A$_{max}$ for conjugated drug) |
| Target Injection Amount | 6-150 μg ADC (no dilution) |

Data collected at 280 nm were integrated using Empower's Apex Track integration method with peak shoulder detection. The retention time integration range is molecule dependent, but is usually within 3-9 minutes. The peak with largest height and area was classified as "native", "main" or "monomer" peak. Any peaks eluting earlier than the "native" peak were classified as "HMW" peaks. Any peaks eluting later than the "native peak" were classified as "LMW" peaks.

The relative percentage of each species was calculated from the ratio of the area of individual peaks to the total area of all peaks. The relative percent area of the following was reported as an indicator of purity: % Total HMW, % Native (or Main or Monomer), and % Total LMW. The total area of all peaks was summed and used in subsequent DAR calculations. However, in some embodiments, only the area of the native peak is used.

Data collected at 252 nm were integrated using Empower's Apex Track integration method with peak shoulder detection. The retention time integration range is molecule dependent, but is usually within 3-9 minutes. The total area of all peaks was summed and used in subsequent DAR calculations. However, in some embodiments, only the area of the native peak is used.

DAR was determined from the total peak area at 280 nm (A$_{max}$ for the ADC) and the total peak area at 252 nm (A$_{max}$ for the drug). Although 252 nm is a common A$_{max}$ for drug conjugates used for ADCs, an appropriate wavelength can be selected for a specific conjugate, e.g., using known methods. The amount of drug bound to the antibody can be determined by the difference in total peak areas at these two wavelengths, using the naked antibody as a reference standard, if applicable.

The following two equations (which were derived from the Beer-Lambert law) were verified and demonstrated consistency.

$$DAR = \frac{\varepsilon_{252\,nm}^{mAb} * \text{Total } Area_{280\,nm} - \varepsilon_{280\,nm}^{mAb} * \text{Total } Area_{252\,nm}}{\varepsilon_{280\,nm}^{drug} * \text{Total } Area_{252\,nm} - \varepsilon_{252\,nm}^{drug} * \text{Total } Area_{280\,nm}} \quad \text{Equation 1}$$

Equation 1 does not require the use of a naked antibody reference standard. However, systematic determination of extinction coefficients (E) for both the antibody and the drug at 252 nm is required. The extinction coefficient at a given wavelength can readily be calculated from the Beer-Lambert law by using a solution of either the antibody or the drug having a known concentration and measuring the absorbance at the given wavelength.

$$DAR = \frac{\varepsilon_{280\,nm}^{mAb}}{\text{Total } Area_{280\,nm}^{mAb}} * \frac{\text{Total } Area_{252\,nm}^{ADC} * \text{Total } Area_{280\,nm}^{mAb} - \text{Total } Area_{280\,nm}^{ADC} * \text{Total } Area_{252\,nm}^{mAb}}{\varepsilon_{252\,nm}^{drug} * \text{Total } Area_{280\,nm}^{ADC} - \varepsilon_{280\,nm}^{drug} * \text{Total } Area_{252\,nm}^{ADC}} \quad \text{Equation 2}$$

Equation 2 does not require extinction coefficient determination for the antibody at 252 nm, but it does require collection of UPLC data for a naked antibody reference standard.

Although UPLC has been exemplified, other size exclusion chromatography techniques can be used in methods described herein. Size exclusion chromatography generally refers to separation of molecules by size, where the chromatographic elution time is characteristic for a particular molecule. Additional methods include, e.g., SEC-HPLC, reversed phase (RP) HPLC, RP-UPLC.

In some embodiments, an ADC sample is not diluted prior to analysis by size exclusion chromatography (e.g., HPLC or UPLC). In some embodiments, an ADC sample does not require dilution prior to analysis by size exclusion chromatography as a total amount of the ADC sample is applied to the size exclusion chromatography matrix. In some embodiments, a sample containing about 1 µg/µL to about 500 µg/µL ADC is analyzed.

Slope Spectroscopy-Based Methods

In some embodiments, DAR is determined by calculating the concentrations of antibody and drug in an ADC sample. For example, slope spectroscopy is a known method for determining the absorbance of a solution at various path lengths. The values of the absorbance at various path lengths can then be used, based on the Beer-Lambert law, to calculate the concentration of a compound in the solution. Methods and systems employing slope spectroscopy are known (see, e.g., US Publ. No. 20120130649) and commercially available (see, e.g., SoloVPE (C Technologies, Inc., Bridgewater, N.J.)). Such methods and systems were adapted to measure concentrations of antibody and drug in ADC preparations, from which a DAR was determined.

For example, an ADC sample can be placed in a vessel; a probe can be moved relative to the vessel such that the probe makes contact with the bottom of the vessel; the probe can be moved relative to the vessel such that the probe moves from the bottom of the vessel through the sample by a predetermined increment such that a preselected path length through the solution is obtained; an absorbance reading can be taken at an absorption maxima for the antibody; the probe can be moved repeatedly relative to the sample and a measurement can be taken; a regression line can be generated from the absorbance and path length such that a slope of the regression line is obtained; and the concentration of the antibody can be determined by dividing the slope of the regression line by the extinction coefficient of the antibody. The steps can then be repeated using the absorption maxima for the drug to determine the concentration of the drug. DAR can be calculated from the determined drug concentration and antibody concentration.

In some embodiments, an ADC sample is not diluted prior to analysis by slope spectroscopy. In some embodiments, a sample containing about 0.1 µg/µL to about 500 µg/µL ADC is analyzed.

Antibody Drug Conjugates

The term "antibody-drug conjugate" as used herein, refers to a protein that is created by linking an antibody to a biologically active cytotoxic payload or drug. Antibody-drug conjugates (ADC) are generally produced through chemical modification/coupling reactions known to those skilled in the art. Any antibody-drug conjugate can be analyzed using the methods described herein.

In some embodiments, an antibody-drug conjugate includes an anti-tumor antibody (see, e.g., Adler et al., Hematol. Oncol. Clin. North Am. 26:447-81 (2012); Li et al., Drug Discov. Ther. 7:178-84 (2013); Scott et al., Cancer Immun. 12:14 (2012); and Sliwkowski et al., Science 341: 1192-1198 (2013)). Table 1 presents a non-comprehensive list of certain human polypeptide antigens targeted by known, available antibody agents, and notes certain cancer indications for which the antibody agents have been proposed to be useful. Any of the antibodies in Table 1 can be included in an antibody-drug conjugate assessed using methods of the disclosure.

TABLE 1

| Human Antigen | Antibody (commercial or scientific name) | Cancer indication |
|---|---|---|
| CD2 | Siplizumab | Non-Hodgkin's Lymphoma |
| CD3 | UCHT1 | Peripheral or Cutaneous T-cell Lymphoma |
| CD4 | HuMax-CD4 | |
| CD19 | SAR3419, MEDI-551 | Diffuse Large B-cell Lymphoma |
| CD19 and CD3 or CD22 | Bispecific antibodies such as Blinatumomab, DT2219ARL | Non-Hodgkin's Lymphoma |
| CD20 | Rituximab, Veltuzumab, Tositumomab, Ofatumumab, Ibritumomab, Obinutuzumab, | B cell malignancies (Non-Hodgkin's lymphoma, Chronic lymphocytic leukemia) |
| CD22 (SIGLEC2) | Inotuzumab, tetraxetan, CAT-8015, DCDT2980S, Bectumomab | Chemotherapy-resistant hairy cell leukemia, Hodgkin's lymphoma |
| CD30 | Brentuximab vedotin | |
| CD33 | Gemtuzumab ozogamicin (Mylotarg) | Acute myeloid leukemia |

TABLE 1-continued

| Human Antigen | Antibody (commercial or scientific name) | Cancer indication |
|---|---|---|
| CD37 | TRU-016 | Chronic lymphocytic leukemia |
| CD38 | Daratumumab | Multiple myeloma, hematological tumors |
| CD40 | Lucatumumab | Non-Hodgkin's lymphoma |
| CD52 | Alemtuzumab (Campath) | Chronic lymphocytic leukemia |
| CD56 (NCAM1) | Lorvotuzumab | Small Cell Lung Cancer |
| CD66e (CEA) | Labetuzumab | Breast, colon and lung tumors |
| CD70 | SGN-75 | Non-Hodgkin's lymphoma |
| CD74 | Milatuzumab | Non-Hodgkin's lymphoma |
| CD138 (SYND1) | BT062 | Multiple Myeloma |
| CD152 (CTLA-4) | Ipilimumab | Metastatic melanoma |
| CD221 (IGF1R) | AVE1642, IMC-A12, MK-0646, R150, CP 751871 | Glioma, lung, breast, head and neck, prostate and thyroid cancer |
| CD254 (RANKL) | Denosumab | Breast and prostate carcinoma |
| CD261 (TRAILR1) | Mapatumumab | Colon, lung and pancreas tumors and haematological malignancies |
| CD262 (TRAILR2) | HGS-ETR2, CS-1008 | |
| CD326 (Epcam) | Edrecolomab, 17-1A, IGN101, Catumaxomab, Adecatumumab | Colon and rectal cancer, malignant ascites, epithelial tumors (breast, colon, lung) |
| CD309 (VEGFR2) | IM-2C6, CDP791 | Epithelium-derived solid tumors |
| CD319 (SLAMF7) | HuLuc63 | Multiple myeloma |
| CD340 (HER2) | Trastuzumab, Pertuzumab, Ado-trastuzumab emtansine | Breast cancer |
| CAIX (CA9) | cG250 | Renal cell carcinoma |
| EGFR (c-erbB) | Cetuximab, Panitumumab, nimotuzumab and 806 | Solid tumors including glioma, lung, breast, colon, and head and neck tumors |
| EPHA3 (HEK) | KB004, IIIA4 | Lung, kidney and colon tumors, melanoma, glioma and haematological malignancies |
| Episialin | Epitumomab | Epithelial ovarian tumors |
| FAP | Sibrotuzumab and F19 | Colon, breast, lung, pancreas, and head and neck tumors |
| HLA-DR beta | Apolizumab | Chronic lymphocytic leukemia, non-Hodkin's lymphoma |
| FOLR-1 | Farletuzumab | Ovarian tumors |
| 5T4 | Anatumomab | Non-small cell lung cancer |
| GD3/GD2 | 3F8, ch14.18, KW-2871 | Neuroectodermal and epithelial tumors |
| gpA33 | huA33 | Colorectal carcinoma |
| GPNMB | Glembatumumab | Breast cancer |
| HER3 (ERBB3) | MM-121 | Breast, colon, lung, ovarian, and prostate tumors |
| Integrin αVβ3 | Etaracizumab | Tumor vasculature |
| Integrin α5β1 | Volociximab | Tumor vasculature |
| Lewis-Y antigen | hu3S193, IgN311 | Breast, colon, lung and prostate tumors |
| MET (HGFR) | AMG 102, METMAB, SCH900105 | Breast, ovary and lung tumors |
| Mucin-1/CanAg | Pemtumomab, oregovomab, Cantuzumab | Breast, colon, lung and ovarian tumors |
| PSMA | ADC, J591 | Prostate Cancer |
| Phosphatidylserine | Bavituximab | Solid tumors |
| TAG-72 | Minretumomab | Breast, colon and lung tumors |
| Tenascin | 81C6 | Glioma, breast and prostate tumours |
| VEGF | Bevacizumab | Tumour vasculature |

In some embodiments, an antibody-drug conjugate includes a drug that is one or more of pro-apoptotic, cytostatic and/or cytotoxic agents, for example specifically including agents utilized and/or recommended for use in treating one or more diseases, disorders or conditions associated with undesirable cell proliferation. In many embodiments, a drug is a chemotherapeutic agent useful in the treatment of cancer. In some embodiments, a chemotherapeutic agent may be or comprise one or more alkylating agents, one or more anthracyclines, one or more cytoskeletal disruptors (e.g., microtubule targeting agents such as taxanes, maytansine and analogs thereof), one or more epothilones, one or more histone deacetylase inhibitors (HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant antiproliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g., DM1), Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof.

In some embodiments, an antibody-drug conjugate assessed using a method of the disclosure is hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, CMC-544, SAR3419, CDX-011, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, IMGN-901, vorsetuzumab mafodotin, or lorvotuzumab mertansine (see, e.g., Sassoon et al., Methods Mol. Biol. 1045:1-27 (2013); Bouchard et al., Bioorganic Med. Chem. Lett. 24: 5357-5363 (2014)).

Applications

Methods of the disclosure have a variety of applications and include, e.g., quality control at different stages of manufacture of a drug substance or drug product, analysis of an ADC preparation prior to and/or after completion of a drug substance or drug product manufacture (e.g., prior to or after distribution to a fill/finish environment or facility), prior to or after release of a drug substance or drug product into commerce (e.g., before distribution to a pharmacy, a caregiver, a patient, or other end-user). In some instances, an ADC preparation is a drug substance (an active pharmaceutical ingredient or "API") or a drug product (an API formulated for use in a subject such as a human patient). In some instances, an ADC preparation is from a stage of manufacture or use that is prior to release to care givers or other end-users; prior to packaging into individual dosage forms, such as syringes, pens, vials, or multi-dose vials; prior to determination that the batch can be commercially released, prior to production of a Certificate of Testing, Material Safety Data Sheet (MSDS) or Certificate of Analysis (CofA) of the preparation.

Assessments from methods described herein are useful for guiding, controlling or implementing a number of activities or steps in the process of making, distributing, and monitoring and providing for the safe and efficacious use of an ADC preparation. Thus, in an embodiment, e.g., responsive to the evaluation, e.g., depending on whether a criterion is met (e.g., a particular DAR, average DAR, and/or DAR range), a decision or step is taken. Methods described herein may include making a decision: (a) as to whether an ADC preparation may be formulated into drug substance or drug product; (b) as to whether an ADC preparation may be reprocessed (e.g., the preparation may undergo a repetition of a previous process step); and/or (c) that the ADC preparation is not suitable for formulation into drug substance or drug product. In some instances, methods comprise: formulating as referred to in step (a), reprocessing as referred to in step (b), or rendering the preparation unusable for commercial release, e.g., by labeling it or destroying it, as referred to in step (c).

What is claimed:

1. A method of determining a ratio of drug to antibody (DAR) in a sample comprising an antibody-drug conjugate, comprising:
applying the sample to a size exclusion chromatography matrix;
detecting absorbance response of the sample at a first light wavelength (λ1), wherein the first light wavelength is a predetermined absorbance maxima of the antibody;
detecting absorbance response of the sample at a second light wavelength (λ2), wherein the second light wavelength is a predetermined absorbance maxima of the drug;
determining a total absorbance of the sample at the first light wavelength and a total absorbance of the sample at the second light wavelength, each total absorbance calculated by integrating peaks of absorbance responses over a time interval by summing an area of high molecular weight (HMW) peaks, low molecular weight (LMW) peaks and a main peak; and,
calculating the DAR using the following Equation 1:

$$DAR = \frac{\varepsilon_{\lambda 2}^{mAb} * \text{Total } Area_{\lambda 1} - \varepsilon_{\lambda 1}^{mAb} * \text{Total } Area_{\lambda 2}}{\varepsilon_{\lambda 1}^{drug} * \text{Total } Area_{\lambda 2} - \varepsilon_{\lambda 2}^{drug} * \text{Total } Area_{\lambda 1}}$$

wherein $\varepsilon_{\lambda 1}^{mAb}$ is an extinction coefficient of the antibody at the first light wavelength; $\varepsilon_{\lambda 2}^{mAb}$ is an extinction coefficient of the antibody at the second light wavelength; $\varepsilon_{\lambda 1}^{drug}$ is an extinction coefficient of the drug at the first light wavelength; $\varepsilon_{\lambda 2}^{drug}$ is an extinction coefficient of the drug at the second light wavelength; Total $Area_{\lambda 1}$ is the total absorbance of the sample at the first light wavelength; and Total $Area_{\lambda 2}$ is the total absorbance of the sample at the second light wavelength.

2. A method of determining a ratio of drug to antibody (DAR) in a first sample comprising an antibody-drug conjugate, comprising:
measuring total absorbance of the first sample comprising the antibody-drug conjugate by:
applying the first sample comprising the antibody-drug conjugate to a size exclusion chromatography matrix;
detecting absorbance response of the first sample at a first light wavelength (λ1), wherein the first wavelength is a predetermined absorbance maxima of the antibody;
detecting absorbance response of the first sample at a second light wavelength (λ2), wherein the second wavelength is a predetermined absorbance maxima of the drug;
determining a total absorbance of the first sample at the first light wavelength and a total absorbance of the first sample at the second light wavelength, each total absorbance calculated by integrating peaks of absorbance responses over a time interval by summing an area of high molecular weight (HMW) peaks, low molecular weight (LMW) peaks and a main peak;
measuring total absorbance of a second sample comprising the antibody by:
applying the second sample comprising the antibody to a size exclusion chromatography matrix;
detecting absorbance response of the second sample comprising the antibody at the first light wavelength (λ1);
detecting absorbance response of the second sample comprising the antibody at the second light wavelength (λ2); and
determining a total absorbance of the second sample comprising the antibody at the first light wavelength and a total absorbance of the second sample at the second light wavelength, each total absorbance calculated by integrating peaks of absorbance responses over a time interval by summing an area of high molecular weight (HMW) peaks, low molecular weight (LMW) peaks and a main peak; and
calculating the DAR using the following Equation 2:

$$DAR = \frac{\varepsilon_{\lambda 1}^{mAb}}{\text{Total } Area_{\lambda 1}^{mAb}} * \frac{\text{Total } Area_{\lambda 2}^{ADC} * \text{Total } Area_{\lambda 1}^{mAb} - \text{Total } Area_{\lambda 1}^{ADC} * \text{Total } Area_{\lambda 2}^{mAb}}{\varepsilon_{\lambda 2}^{drug} * \text{Total } Area_{\lambda 1}^{ADC} - \varepsilon_{\lambda 1}^{drug} * \text{Total } Area_{\lambda 2}^{ADC}}$$

wherein $\varepsilon_{\lambda1}^{mAb}$ is an extinction coefficient of the antibody at the first light wavelength; $\varepsilon_{\lambda1}^{drug}$ is an extinction coefficient of the drug at the first light wavelength; $\varepsilon_{\lambda2}^{drug}$ is an extinction coefficient of the drug at the second light wavelength; Total $\text{Area}_{\lambda1}^{mAb}$ is the total absorbance of the second sample comprising the antibody at the first light wavelength; Total $\text{Area}_{\lambda2}^{mAb}$ is the total absorbance of the second sample comprising the antibody at the second light wavelength; Total $\text{Area}_{\lambda1}^{ADC}$ is the total absorbance of the first sample comprising the antibody-drug conjugate at the first light wavelength; and Total $\text{Area}_{\lambda2}^{ADC}$ is the total absorbance of the first sample comprising the antibody-drug conjugate at the second light wavelength.

3. The method of claim 1, further comprising:
calculating the extinction coefficient of the antibody at the first light wavelength or at the second light wavelength based on absorbance of a solution of the antibody with a known concentration.

4. The method of claim 1, further comprising:
calculating the extinction coefficient of the drug at the first light wavelength or at the second light wavelength based on absorbance of a solution of the drug with a known concentration.

5. The method of claim 1, wherein the size exclusion chromatography, comprises ultra-performance liquid chromatography (UPLC), a reversed phase (RP) UPLC, or a high performance liquid chromatography (HPLC).

6. The method of claim 1, wherein the sample includes 1 to 500 µg/µL of antibody-drug-conjugate (ADC).

7. The method of claim 1, wherein the antibody is an anti-tumor antibody.

8. The method of claim 1, wherein the drug is a pro-apoptotic, cytostatic or cytotoxic agent.

9. The method of claim 1, wherein integrating peaks of absorbance responses includes detecting a peak shoulder of each peak of absorbance response.

10. The method of claim 1, wherein the time interval is between 3 to 9 minutes.

11. The method of claim 2, further comprising:
calculating the extinction coefficient of the antibody at the first light wavelength or at the second light wavelength based on absorbance of a solution of the antibody with a known concentration.

12. The method of claim 2, further comprising:
calculating the extinction coefficient of the drug at the first light wavelength or at the second light wavelength based on absorbance of a solution of the drug with a known concentration.

13. The method of claim 2, wherein the size exclusion chromatography comprises ultra-performance liquid chromatography (UPLC), a reversed phase (RP) UPLC, or high performance liquid chromatography (HPLC).

14. The method of claim 2, wherein the first sample includes 1 µg/µL to 500 µg/µL of antibody-drug-conjugate (ADC).

15. The method of claim 2, wherein the antibody is an anti-tumor antibody.

16. The method of claim 2, wherein the drug is a pro-apoptotic, cytostatic or cytotoxic agent.

17. The method of claim 2, wherein integrating peaks of absorbance responses includes detecting peak shoulder of each peak of absorbance response.

18. The method of claim 2, wherein the time interval is between 3 to 9 minutes.

* * * * *

UNITED STATES PATENT AND TRADEMARK OFFICE
CERTIFICATE OF CORRECTION

PATENT NO. : 10,976,241 B2
APPLICATION NO. : 16/121909
DATED : April 13, 2021
INVENTOR(S) : Andria Skinner et al.

It is certified that error appears in the above-identified patent and that said Letters Patent is hereby corrected as shown below:

On the Title Page

"(60) Provisional application No. 62/566,153, filed on Sep. 8, 2017."
Should read:
-- (60) Provisional application No. 62/556,153, filed on Sep. 8, 2017. --

In the Claims

At Column 8, Claim number 1, Line numbers 11-12:
"wherein $\varepsilon_{\lambda 1}^{mAb}$ is an extinction coefficient of the antibody at the first light wavelength; $\varepsilon_{\lambda 2}^{mAb}$ is an extinction"
Should read:
-- wherein $\varepsilon_{\lambda 1}^{mAb}$ is an extinction coefficient of the antibody at the first light wavelength; $\varepsilon_{\lambda 2}^{mAb}$ is an extinction --

At Column 8, Claim number 1, Line numbers 14-15:
"length; $\varepsilon_{\lambda 1}^{drug}$ is an extinction coefficient of the drug at the first light wavelength; $\varepsilon_{\lambda 2}^{drug}$ is an extinction coef-"
Should read:
-- length; $\varepsilon_{\lambda 1}^{drug}$ is an extinction coefficient of the drug at the first light wavelength; $\varepsilon_{\lambda 2}^{drug}$ is an extinction coef- --

At Column 9, Claim number 2, Line numbers 1-2:
"wherein $\varepsilon_{\lambda 1}^{mAb}$ is an extinction coefficient of the antibody at the first light wavelength; $\varepsilon_{\lambda 1}^{drug}$ is an extinction"

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,976,241 B2

Should read:
-- wherein $\varepsilon_{\lambda 1}^{mAb}$ is an extinction coefficient of the antibody at the first light wavelength; $\varepsilon_{\lambda 1}^{drug}$ is an extinction --

At Column 9, Claim number 2, Line numbers 4-5:
"$\varepsilon_{\lambda 2}^{drug}$ is an extinction coefficient of the drug at the second light wavelength; Total Area$_{\lambda 1}^{mAb}$ is the total"
Should read:
-- $\varepsilon_{\lambda 2}^{drug}$ is an extinction coefficient of the drug at the second light wavelength; $\text{Total Area}_{\lambda 1}^{mAb}$ is the total --

At Column 9, Claim number 2, Line number 7:
"body at the first light wavelength; Total Area$_{\lambda 2}^{mAb}$ is"
Should read:
-- body at the first light wavelength; $\text{Total Area}_{\lambda 2}^{mAb}$ is --

At Column 9, Claim number 2, Line number 10:
"Area$_{\lambda 1}^{ADC}$ is the total absorbance of the first sample"
Should read:
-- $\text{Area}_{\lambda 1}^{ADC}$ is the total absorbance of the first sample --

At Column 9, Claim number 2, Line number 12:
"light wavelength; and Total Area$_{\lambda 2}^{ADC}$ is the total"
Should read:
-- light wavelength; and $\text{Total Area}_{\lambda 2}^{ADC}$ is the total --

At Column 9, Claim number 6, Line number 29:
"6. The method of claim 1, wherein the sample includes 1"
Should read:
-- 6. The method of claim 1, wherein the sample includes 1 μg/μL --